US009451765B2

(12) United States Patent
Cuer et al.

(10) Patent No.: US 9,451,765 B2
(45) Date of Patent: Sep. 27, 2016

(54) BIOLOGICAL DECONTAMINATION GEL AND METHOD FOR DECONTAMINATING SURFACES BY USING THIS GEL

(75) Inventors: Frederic Cuer, Cornillon (FR); Sylvain Faure, Venasque (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 520 days.

(21) Appl. No.: 13/806,856

(22) PCT Filed: Jun. 29, 2011

(86) PCT No.: PCT/EP2011/060914
§ 371 (c)(1),
(2), (4) Date: Feb. 19, 2013

(87) PCT Pub. No.: WO2012/001046
PCT Pub. Date: Jan. 5, 2012

(65) Prior Publication Data
US 2013/0171024 A1 Jul. 4, 2013

(30) Foreign Application Priority Data
Jul. 2, 2010 (FR) .................................... 10 55399

(51) Int. Cl.
*A61L 2/00* (2006.01)
*A01N 59/00* (2006.01)
*A01N 25/04* (2006.01)
*A61L 2/23* (2006.01)

(52) U.S. Cl.
CPC ........ *A01N 25/04* (2013.01); *A61L 2/23* (2013.01)

(58) Field of Classification Search
CPC .................................. A01N 25/04; A61L 2/23

USPC ............................................. 422/28; 424/722
See application file for complete search history.

(56) References Cited

U.S. PATENT DOCUMENTS 6,455,751 B1    9/2002    Hoffman et al.
7,026,274 B2    4/2006    Jenevein
(Continued)

FOREIGN PATENT DOCUMENTS

FR    2827530 A1    1/2003
FR    2891470 A1    4/2007
(Continued)

OTHER PUBLICATIONS

English Translation of International Publication No. WO 2010/037809 A1 provided by espace.net: Cuer; Process for the Electrokinetic Decontamination of a Porous Solid Medium; Apr. 8, 2010.*
(Continued)

*Primary Examiner* — Kevin Joyner
(74) *Attorney, Agent, or Firm* — Hultquist, PLLC; Mary B. Grant

(57) ABSTRACT

A biological decontamination gel, consisting of a colloidal solution comprising from 5 to 30% by mass, preferably 5 to 25% by mass, still preferably 8 to 20% by mass, based on the mass of the gel, of at least one inorganic viscosifying agent: 0.5 to 10 mol/L of gel, preferably 1 to 10 mol/L of gel, of at least one active biological decontamination agent; 0.05 to 5% by mass, preferably 0.05 to 2% by mass, based on the mass of the gel, of at least one super-absorbent polymer; 0.1 to 2% by mass, based on the mass of the gel, of at least one surfactant; and the remainder of solvent.
A biological decontamination method applying this gel.

30 Claims, 6 Drawing Sheets

(56) References Cited

U.S. PATENT DOCUMENTS

| | | |
|---|---|---|
| 7,083,806 B2 | 8/2006 | Rippon et al. |
| 7,713,357 B2 | 5/2010 | Faure et al. |
| 7,718,010 B2 | 5/2010 | Faure et al. |
| 2003/0109017 A1 | 6/2003 | Conerly et al. |
| 2004/0022867 A1 | 2/2004 | Tucker et al. |
| 2006/0073067 A1 | 4/2006 | Schilling et al. |
| 2008/0228022 A1 | 9/2008 | Faure et al. |
| 2010/0069281 A1 | 3/2010 | Guignot et al. |
| 2011/0186444 A1 | 8/2011 | Cuer et al. |
| 2012/0021068 A1* | 1/2012 | Barness et al. ............... 424/661 |

FOREIGN PATENT DOCUMENTS

| | | |
|---|---|---|
| WO | 0185845 A1 | 11/2001 |
| WO | 03008529 A1 | 1/2003 |
| WO | 2007039598 A2 | 4/2007 |
| WO | WO 2010037809 A1 * | 4/2010 |

OTHER PUBLICATIONS

Harper, B., et al., "A Comparison of Decontamination Technologies for Biological Agents on Selected Commercial Surface Materials", "Domestic Preparedness", Apr. 2001, Publisher: U.S. Army Soldier and Biological Chemical Command.

Josse, D., et al, "Decontamination Cutanee Vis-a-Vis des Agents Organophoshpores et de l'Yperite au Soufre: Bilan et perspectives", "Medecine et Armees", Feb. 2006, pp. 33-36 (English Abstract), vol. 34, No. 1.

Rogers, J., et al., "Decontamination assessment of Bacillus anthracis, Bacillus subtilis, and Geobacillus stearothermophilus spores on indoor surfaces using a hydrogen peroxide gas generator", "J. Appl. Microbiol.", 2005, pp. 739-748, vol. 99, No. 4.

* cited by examiner

BIOLOGICAL DECONTAMINATION GEL AND METHOD FOR DECONTAMINATING SURFACES BY USING THIS GEL

CROSS-REFERENCE TO RELATED APPLICATIONS

This application is a U.S. national phase under the provisions of 35 U.S.C. §371 of International Patent Application No. PCT/EP11/60914 filed Jun. 29, 2011, which in turn claims priority of French Patent Application No. 1055399 filed Jul. 2, 2010. The disclosures of such international patent application and French priority patent application are hereby incorporated herein by reference in their respective entireties, for all purposes.

TECHNICAL FIELD

The object of the present invention is a biological decontamination gel which may be used for decontaminating surfaces.

The present invention further relates to a method for decontaminating surfaces by using this gel.

The invention applies to decontamination of surfaces polluted, contaminated by biological agents.

The method according to the invention may be applied to any kind of surfaces such as metal surfaces, plastic material surfaces, glassy material surfaces.

The invention most particularly applies to the surfaces of porous materials such as cement matrices, materials, such as slurries, mortars and concretes; bricks; plasterwork; and stone.

The technical field of the invention may thus be generally defined as that of the decontamination of surfaces with view to removing therefrom pollutants, contaminants which are found thereon and the presence of which on these surfaces is not desired.

More particularly, the technical field of the invention is that of biological decontamination of contaminated surfaces, notably contaminated with toxic biological species such as for example, endospores, toxins, viruses.

STATE OF THE PRIOR ART

For about ten years, the succession of terrorist chemical and more recently biological acts, for example the attack with sarin gas in the Tokyo Underground in 1995, the suicide bombings of the Twin Towers of New York in 2001, the anthrax from the US Postal Service mail in the United States in 2001, and the explosives attacks in the Madrid railway stations in 2004, have incited many countries to build real research programs for providing themselves with efficient means against terrorist threats.

The agents of the threat essentially of a chemical nature at the beginning of the $20^{th}$ century, have evolved towards weapons with stronger impact, more simple to apply and especially non-detectable before the occurrence of the first body symptoms.

Fear is therefore today focused on terrorist attacks of the biological type which are particularly contagious orally. Toxic biological species such as *Bacillus anthracis* (anthrax) or further Botulinum toxin are considered as weapons for which the likelihood of use is the highest.

In the case of biological decontamination, two goals are sought:
the first is to inactivate biological, bio-toxic contaminants during prolonged contact between the biocidal agent (generally a strongly oxidizing chemical species) and the pathogenic agent. This inhibition phase requires a contact time which may attain several hours depending on the formulation used,
the second is to most often try to transfer the contamination species to a solid or liquid phase allowing the inactivated species to be removed from the treated material.

Generally, the techniques for cleaning up the materials contaminated by a biological contamination consist in putting a liquid containing a biocidal agent in contact with the contaminated surfaces. The application of the biocidal solution is generally achieved by spraying or by washing either coupled or not with a mechanical effect such as brushing.

Thus, document [1] describes a cleaning composition for removing antibacterial agents and other agents used in the decontamination following a biological attack. This composition notably comprises ethanol, isopropanol, ethylene glycol n-hexyl ether, a bromide and a chloride.

Document [2] describes a large scale decontamination method in which a solid, stable peracid or a solid, stable source of peracid is put into contact with a contaminated surface.

More recently, with new wetting techniques by nebulization or by projection of foam, it has been possible to reduce the amount of biocidal solutions used and therefore the volume of produced chemical effluents. In this respect, reference may be made to documents [3] and [4].

Other methods use biocidal agents in gaseous form such as hydrogen peroxide or further ozone, as this is the case of the method described in document [5].

The major drawback associated with these methods is however the risk of dissemination of toxic agents into the environment, whether these are biological and chemical toxic agents in the case of the liquid spraying method, or else of chemical toxic agents in the case of the method applying biocidal agents in gaseous form.

Further, the method which applies biocidal agents in gaseous form, is exclusively efficient when it is applied in closed enclosures.

In order to meet the problem of recovering the contamination, a third category of method has been developed more recently.

In these methods, the transfer of the contamination is accomplished towards a solid supporting material capable of trapping and/or destroying toxic biological species. The thereby generated waste is then also found in solid form. Obtaining a solid waste is particularly of interest in order to limit the risks of spreading of the toxic agents into the environment but also for facilitating management and treatment of the produced waste.

Different technologies applying a solid support material have now been already developed. These are: first of all, the so-called <<dusting glove>> technology intended for decontaminating persisting toxic liquids found on the skin or on pieces of equipment.

In this glove, the decontaminating agent is an absorbent powder, generally Fuller's earth. The latter is poured onto the contaminated location by tapping, it absorbs the toxic liquid and then it is wiped off by means of the sponge side of the glove [6].

The composition of the glove may, in certain cases, include an oxidizer, oxidizing agent, capable of inactivating the contamination trapped by Fuller's earth. This technique, particularly suitable for the care of persons, remains nevertheless limited to the treatment of liquid contaminations on a small scale.

Other decontamination products, which appear as a gel, generate a solid waste and thus give the possibility of doing without the use of liquid solutions for cleaning up rooms with large surfaces and with complex geometries.

These gels are generally applied by spraying them on the surface to be decontaminated.

After a contact time of the gel with the surface to be decontaminated, equivalent to the evaporation time of the solvent, the obtained dry waste is removed by brushing and/or suction. The major benefit of these methods is their capability of treating large surfaces and uneven geometries.

Thus, document [7] describes a gel composition containing oxidizing agents for chemical or biological decontamination of contaminated areas. This composition is prepared by adding thickeners or gelling agents in the form of colloids to an oxidizing agent solution in order to form a viscous colloidal gel.

This solution may be an aqueous or organic solution.

The thickeners or gelling agents may be selected from silica, alumina, aluminosilicates, mixtures of silica and alumina, and clays such as smectite.

The oxidizing agents are notably sodium hypochlorite, ammonium persulfate, or hydrogen peroxide.

It is indicated that these gels may be used for removing biological agents such as microorganisms like bacteria, fungi, viruses and spores, or chemical agents such as neurotoxic gases.

The gels are then sprayed on the surface to be treated and then recovered by suction after drying.

It is indicated that an oxidizing gel containing potassium peroxymonosulfate and 15% of Cab-O—Sil® EH-5 silica as a gelling agent, destroys <<Mustard>>, <<VX>> and <<GD>> chemical agents within the time required for bringing the gel to dryness and that *Bacillus globigii* (BG), simulating anthrax, is also partly destroyed by this gel.

The gelled formulations developed by the Lawrence Livermore National Laboratory under the names of L-Gel 115, and L-Gel 200 are similar to the formulations developed in document [7] and are applied with the so-called <<L-Gel>> method. This method seems to have some efficiency towards biological contamination such as a contamination by spores of *Bacillus globigii* [8].

These gels are formulated from oxidizing acid solutions to which are added organic solvents and a silica filler. The gels are then sprayed on the surfaces to be treated and then recovered by suction after drying. Among the critical points of this method, the presence of powerful oxidizing agents first appears, the chemical stability of which is often very limited in time.

Moreover, in order to avoid runoffs, in particular when the gel is applied on walls or ceilings, the latter is applied in the form of very thin films with a thickness which does not exceed 125 µm in document [7]. The result of this is a powdery dry waste which may cause, if the efficiency of the treatment is not total, dissemination of the biotoxic and chemical species, such as oxidizing compounds, into the atmosphere.

The performances of the method, determine towards a contamination by anthrax in the form of an aerosol ($10^7$ and $10^8$ spores per sample of 0.16 m²), show that it does not allow a reduction in the contamination of more than 4 decades [8].

Moreover, in the case of nuclear decontamination, gelled formulations with which it is possible to get rid of problems related to the powdery nature of the dry waste and to increase the efficiency of the gel method are the subject of documents [9] and [10]. The gel formulations which are described therein give the possibility of releasing by means of low erosion of the supporting material, the contamination in particulate form. The contaminant is then found trapped in the dry gel residue [9], [10].

These gels are specifically intended for radioactive decontamination and are by no means adapted or able to be adapted to the biological decontamination of surfaces.

Further, the gels described above do not allow decontamination in depth of porous material.

Therefore there exists, with regard to the foregoing, a need for a biological decontamination gel which produces dry wastes which are easy to remove without dissemination of biological contaminants, with which it is possible to treat with the same efficiency a large variety of surfaces regardless of their shape, their geometry, their size and their nature.

In particular there exists a need for a biological decontamination gel which allows efficient decontamination of porous surfaces notably mineral surfaces and which ensures decontamination in depth of such surfaces over a depth which may attain several millimeters for example.

Further there exists a need for a decontamination gel which does not produce any chemical, mechanical or physical alteration of the treated surfaces.

The goal of the present invention is to provide a biological decontamination gel which inter alia meets this need.

The goal of the present invention is further to provide a decontamination gel which does not have the drawbacks, defects, limitations and disadvantages of the decontamination gels of the prior art and which solves the problems of the decontamination gels of the prior art.

DISCUSSION OF THE INVENTION

This goal, and further other ones, are achieved, according to the invention with a biological decontamination gel, consisting of a colloidal solution comprising, preferably consisting of:

- 5 to 30% by mass, preferably 5 to 25% by mass, still preferably 8 to 20% by mass based on the mass of the gel, of at least one inorganic viscosifying agent;
- 0.5 to 10 mol/L of gel, preferably 1 to 10 mol/L of gel, of at least one biological decontamination active agent;
- 0.05 to 5% by mass, preferably 0.05 to 2% by mass based on the mass of the gel, of at least one super-absorbent polymer;
- 0.1 to 2% by mass based on the mass of the gel, of at least one surfactant;

and the remainder of solvent.

The gels according to the invention have never been described in the prior art.

In particular, the incorporation of a super-absorbent polymer in a decontamination gel and a fortiori the combination in such a gel of such a super-absorbent polymer with a biological decontamination agent has never been described in the prior art, notably as represented by the documents mentioned above.

The gels according to the invention meet the whole of the needs mentioned above, they do not have the drawbacks, defects, limitations and disadvantages of the gels of the prior art, such as those described in the documents mentioned above.

The gels according to the invention solve the problems exhibited by the biological decontamination gels of the prior art without having the drawbacks thereof while retaining all the known advantageous properties of these gels.

The gel according to the invention is a colloidal solution, which means that the gel according to the invention contains mineral, inorganic, solid particles of a viscosifying agent, the primary elementary particles of which have a size generally from 2 to 200 nm.

Because of the application of a generally exclusively inorganic viscosifying agent, without any organic viscosifying agent, the organic material content of the gel according to the invention is generally less than 4% by mass, preferably less than 2% by mass, which further is another advantage of the gels according to the invention.

These inorganic, mineral, solid particles play the role of a viscosifier for allowing the solution, for example the aqueous solution to gel and thus adhere to the surfaces to be treated, decontaminated, regardless of their geometry, their shape, their size and of where the contaminants to be removed are found.

Advantageously, the inorganic viscosifying agent may be selected from aluminas, silicas, aluminosilicates, clays such as smectite, and mixtures thereof.

In particular, the inorganic viscosifier may be selected from aluminas ($Al_2O_3$) and silicas ($SiO_2$).

The inorganic viscosifier may only comprise one single silica or alumina or a mixture of the latter, i.e. a mixture of two or more different silicas ($SiO_2/SiO_2$ mixture), a mixture of two or more different aluminas ($Al_2O_3/Al_2O_3$ mixture), or further a mixture of one or more silicas with one or more aluminas ($SiO_2/Al_2O_3$ mixture).

Advantageously, the inorganic viscosifying agent may be selected from pyrogenated silicas, precipitated silicas, hydrophilic silicas, hydrophobic silicas, acid silicas, basic silicas such as the silica Tixosil 73 (trademark) marketed by Rhodia, and mixtures thereof.

Among acid silicas, mention may notably be made of pyrogenated or fumed silicas "Cab-O-Sil" M5, H5 or EH5 (trademarks) marketed by CABOT, and pyrogenated silicas marketed by DEGUSSA under the name of AEROSIL (trademarks).

Among these pyrogenated silicas, the silica AEROSIL 380 (trademark) with a specific surface area of 380 $m^2/g$ will further be preferred, which provides maximum viscosifying properties for a minimal mineral load.

The silica used may also be a so-called precipitated silica obtained for example via a wet route by mixing a soda silicate solution and an acid. The preferred precipitated silicas are marketed by DEGUSSA under the names of SIPERNAT 22 LS and FK 310 (trademarks) or further by Rhodia under the name of TIXOSIL 331 (trademark), the latter is a precipitated silica for which the average specific surface area is comprised between 170 and 200 $m^2/g$.

Advantageously, the inorganic viscosifying agent consists of a mixture of a precipitated silica and of a pyrogenated silica.

The alumina may be selected from calcinated aluminas, milled calcined aluminas, and mixtures thereof.

As an example, mention may be made of the product sold by DEGUSSA under the trade name of <<Aeroxide Alumine C>> which is fine pyrogenated alumina.

Advantageously, according to the invention, the viscosifying agent consists of one or more alumina(s) generally representing 5% to 30% by mass based on the mass of the gel.

In this case, the alumina is preferably at a concentration of 8 to 17% by mass based on the total mass of the gel in order to ensure drying of the gel at a temperature comprised between 20° C. and 50° C. and at a relative humidity comprised between 20 and 60% on average within 30 minutes to 5 hours.

The nature of the mineral viscosifying agent notably when it consists of one or more alumina(s), unexpectedly influences the drying of the gel according to the invention and the grain size of the obtained residue.

Indeed, the dried gel appears as particles with a controlled size, more specifically millimetric solid flakes, the size of which will generally range from 1 to 10 mm, preferably from 2 to 5 mm notably due to the use of the aforementioned compositions of the present invention, in particular when the viscosifying agent consists of by one or more alumina(s).

Let us specify that the size of the particles generally corresponds to their largest dimension.

The gel according to the invention contains an active biological decontamination agent.

By biological decontamination agent which may also be described as a biocidal agent, is meant any agent, which when it is put into contact with a biological species and notably a toxic biological species is capable of inactivating or destroying the latter.

By biological species is meant any type of microorganism such as bacteria, fungi, yeasts, viruses, toxins, spores notably spores of *Bacillus Anthracis*, and protozoans.

The biological species which are removed, destroyed, inactivated by the gel according to the invention are essentially bio-toxic species such as pathogenic spores, like for example the spores of *Bacillus Anthracis*, toxins such as for example Botulinum toxin, and viruses.

The active biological decontamination agent may be selected from bases such as sodium hydroxide, potassium hydroxide, and mixtures thereof; acids such as nitric acid, phosphoric acid, hydrochloric acid, sulfuric acid, and mixtures thereof; oxidizing agents such as peroxides, permanganates, persulfates, ozone, hypochlorites, and mixtures thereof; quaternary ammonium salts such as hexacetylpyridinium salts like hexacetylpyridinium chloride; and mixtures thereof (see especially Examples 1 and 2).

Certain active decontamination agents may be classified among several of the categories defined above.

Thus, nitric acid is an acid but also an oxidizing agent.

The active decontamination agent, such as a biocidal agent, is generally used at a concentration comprised between 0.5 and 10 mol/L of gel, and preferably from 1 to 10 mol/L of gel in order to guarantee a biological species inhibiting power, notably a biotoxic species inhibiting power, compatible with the drying time of the gel, and in order to ensure for example drying of the gel at a temperature comprised between 20° C. and 50° C. and at a relative humidity comprised between 20 and 60% on average within 30 minutes to 5 hours.

The active decontamination agent may be an acid or a mixture of acids. These acids are generally selected from mineral acids such as hydrochloric acid, nitric acid, sulfuric acid and phosphoric acid.

A particularly preferred biological decontaminating agent is nitric acid.

Indeed, in a totally surprising way, it was found that nitric acid destroyed, inactivated biological, notably biotoxic species.

In particular, it was surprisingly shown that nitric acid ensured the destruction, the inactivation of spores such as the spores of *Bacillus thuringiensis* which are particularly resistant species.

The acid(s) is(are) preferably present at a concentration from 0.5 to 10 mol/L, still preferably from 1 to 10 mol/L, in order to ensure drying of the gel generally at a temperature comprised between 20° C. and 50° C. and at a relative humidity comprised between 20 and 60% on average within 30 minutes to 5 hours.

For this type of acidic gel, the inorganic viscosifying agent is preferably silica or a mixture of silicas.

Or else, the active biological decontamination agent may be a base, preferably a mineral base, preferably selected from soda, potash and mixtures thereof.

In the case of such a basic gel formulation, the gel according to the invention has a degreasing action in addition to the decontamination action.

In order to attain total efficiency, including under the most unfavorable weather conditions towards the drying time of the gel, the gel according to the invention may have a wide range of concentrations of basic decontamination agent(s).

Indeed, the increase in the concentration of basic decontamination agents like NaOH or KOH, generally playing the role of a biocidal agent, gives the possibility of considerably increasing the rates for inhibiting biological species, as this was demonstrated for spores of *Bacillus thuringiensis* (Example 2).

The base is advantageously present at a concentration of less than 10 mol/L, preferably between 0.5 and 7 mol/L, still preferably between 1 and 5 mol/L in order to ensure drying of the gel at a temperature comprised between 20° C. and 50° C. and at a relative humidity comprised between 20 and 60% on average within 30 minutes to 5 hours.

For this type of alkaline, basic, gel, the inorganic viscosifying agent is preferably an alumina or a mixture of aluminas.

In order to result in the maximum efficiency over a wide range of materials while guaranteeing the innocuity of the treatment, the biological decontamination agent is preferably sodium hydroxide or potassium hydroxide.

In the case of a treatment of a cement matrix, the basic pH of the gel, which is induced by the use of soda or potash, gives the possibility of avoiding acid-basic-reactions, between the material to be decontaminated and the gel, which are detrimental to the integrity of the gel on the surface and therefore to the efficiency of the method.

The hygroscopicity of sodium hydroxide or potassium hydroxide is also a considerable asset for slowing down the drying phenomenon of the gel. The contact time between the gel according to the invention, for example containing a biocidal solution, and the biological contamination, is then found to be considerably increased.

Indeed, the competition between the evaporation process of the aqueous phase and that of water uptake by the sodium hydroxide or potassium hydroxide crystals favorably modifies the drying kinetics of the gel (Example 3).

With regard to the kinetics for inhibiting the spores (Example 2) and to the drying times of the gels depending on the temperature (Example 4), the biocidal agent will preferably be sodium hydroxide at a concentration comprised between 1 and 5 mol/L.

The gel according to the invention further contains as a fundamental component, a super-absorbent polymer.

By <<super-absorbent polymer>> also designated as <<SAP>>, is generally meant a polymer capable in the dry condition, state, of spontaneously absorbing at least 10 times, preferably at least 20 times its weight of aqueous liquid, in particular of water and notably of distilled water.

Some <<SAPs>> may absorb up to and even more than 1,000 times their weight of liquid.

Such super-absorbent polymers are notably described in the text book <<*Absorbent Polymer Technology, Studies in Polymer Science* 8>> of L. BRANNON-PAPPAS and R. HARLAND, Elsevier editions, 1990, to which reference may be made.

By spontaneous absorption, is meant an absorption time ranging up to about one hour.

The super-absorbent polymer may have a water absorption capacity ranging from 10 to 2,000 times its own weight, preferably from 20 to 2,000 times its own weight (i.e. 20 g to 2,000 g of water absorbed per gram of absorbent polymer), still preferably from 30 to 1,500 times, and in particular from 50 to 1,000 times.

These water absorption characteristics are meant under normal conditions of temperature (25° C.) and of pressure (760 mm Hg i.e. 100,000 Pa) and for distilled water.

The SAP of the biological decontamination gel according to the invention may be selected from sodium poly(meth) acrylates, starches grafted with a (meth)acrylic polymer, hydrolyzed starches grafted with a (meth)acrylic polymer; starch, gum, and cellulose derivative based polymers; and mixtures thereof.

More specifically, the SAP which may be used in the gel according to the invention may for example be selected from:

- polymers resulting from polymerization with partial cross-linking of water-soluble monomers with ethylenic unsaturation, such as acrylic, methacrylic polymers (notably stemming from the polymerization of acrylic and/or methacrylic acid and/or of acrylate and/or methacrylate monomers) or vinyl polymers, in particular cross-linked and neutralized poly(meth)acrylates, notably as a gel; and salts, notably alkaline salts such as the sodium or potassium salts of these polymers;
- starches grafted with polyacrylates;
- acrylamide/acrylic acid copolymers, notably in the form of sodium or potassium salts;
- acrylamide/acrylic acid-grafted starches, notably in the form of sodium or potassium salts;
- sodium or potassium salts of carboxymethylcellulose;
- salts, notably alkaline salts, of cross-linked polyaspartic acids;
- salts, notably alkaline salts of cross-linked polyglutamic acids.

In particular, as an <<SAP>>, a compound may be used, selected from:

- cross-linked sodium or potassium polyacrylates sold under the names of SALSORB CL 10, SALSORB CL 20, FSA type 101, FSA type 102 (Allied Colloids); ARASORB S-310 (Arakawa Chemical); ASAP 2000, Aridall 1460 (Chemdal); KI-GEL 201-K (Siber Hegner); AQUALIC CA W3, AQUALIC CA W7, AQUALIC CA W10; (Nippon Shokuba); AQUA KEEP D 50, AQUA KEEP D 60, AQUA KEEP D 65, AQUA KEEP S 30, AQUA KEEP S 35, AQUA KEEP S 45, AQUA KEEP A1 M1, AQUA KEEP A1 M3, AQUA KEEP HP 200, NORSOCRYL S 35, NORSOCRYL FX 007 (Arkema); AQUA KEEP 10SH-NF, AQUA KEEP J-550 (Kobo); LUQUASORB CF, LUQUASORB MA 1110, LUQUASORB MR 1600, HYSORB C3746-5 (BASF); COVAGEL (Sensient technologies), SANWET IM-5000D (Hoechst Celanese);
- starch-grafted polyacrylates sold under the names of SANWET IM-100, SANWET IM-3900, SANWET IM-50005 (Hoechst);
- starch-grafted acrylamide/acrylic acid copolymers in the form of a sodium or potassium salt sold under the names of WATERLOCK A-100, WATERLOCK A-200, WATERLOCK C-200, WATERLOCK D-200, WATERLOCK B-204 (Grain Processing Corporation);

acrylamide/acrylic acid copolymers in the form of a sodium salt sold under the name of WATERLOCK G-400 (Grain Processing Corporation);

carboxymethylcellulose said under the names of AQUA-SORB A250 (Aqualon;

cross-linked sodium polyglutamate said under the name of GELPROTEIN (Idemitsu Technofine).

Super-absorbent polymers, in particular the super-absorbent polymers (polyelectrolytes) which contain alkaline ions such as sodium or potassium ions, for example of the sodium or potassium poly(meth)acrylate type, impart many properties to the decontamination gels.

First of all, they influence the rheology of the product, notably its flowing threshold. In terms of application of the method, the interest is to guarantee that the gel is perfectly maintained on the treated materials, notably on vertical surfaces and ceilings when the sprayed gel thickness is greater than 1 mm.

Within the scope of a biological decontamination method by a gel, the super-absorbent polymer is of particular interest since it absorbs via a hydrogen bond a portion of the solution, for example of the biocidal solution contained in the gel. As the number of hydrogen bonds formed between the solution, for example the biocidal solution, of the gel and the super-absorbent polymer such as sodium polyacrylate, is dependent on the salt load, absorption/desorption phenomena occur when the salt load of the decontamination gel is modified.

This mechanism is then of particular interest when the question is to decontaminate mineral and porous materials such as cement matrices for example.

Indeed, in contact with the material, the salt load of the gel increases because of the presence of mineral particles very often based on calcium. Within the super-absorbent polymer such as sodium polyacrylate, substitution of the counter-ion $Na^+$ with $Ca^{2+}$ from calcium instantaneously generates a desalting phenomenon of the solution, for example of the biocidal solution, because of the more significant steric hindrance of the calcium ion.

The amount of biocidal solution released by the super-absorbent polymer such as sodium polyacrylate may then instantaneously diffuse into the porosity of the material and penetrate it in depth.

The diffusion phenomenon of the decontamination agent, for example of the biocidal agent towards the core of the material, is much more limited in the case of a gel not containing any super-absorbent polymer (see Example 6).

By adding a super-absorbent polymer to the gel according to the invention, it is therefore possible to significantly increase the efficiency of the gel and of the method according to the invention in the presence of porous materials contaminated in depth over a thickness from one to several millimeters, for example up to 2, 5, 10, 20 or even 100 millimeters (Example 6).

The super-absorbent polymer may preferably be selected from the ranges Aquakeep® or Norsocryl® series marketed by ARKEMA.

The gel may also contain a surfactant or a mixture of surfactants, preferably selected from the family of non-ionic surfactants such as block copolymers like block copolymers of ethylene oxide and propylene oxide, and ethoxylated fatty acids and their mixtures.

For this type of gel, the surfactants are preferably block copolymers marketed by BASF under the name of "PLURONIC®".

The Pluronics® are block copolymers of ethylene oxide and propylene oxide.

These surfactants influence the rheological properties of the gel, notably the thixotropic nature of the product and the recovery time, in order to make it sprayable on floors, walls or ceilings as well by avoiding the occurrence of runoff.

Moreover with surfactants, it is possible to control the adhesion of the dry waste [Example 7] and to control the size of the dry residue flakes for guaranteeing the non-pulverulence of the waste [Example 8].

The solvent according to the invention is generally selected from water, organic solvents and mixtures thereof.

A preferred solvent is water, and in this case, the solvent consists therefore of water, comprises 100% water.

The invention further relates to a method for biological decontamination of a surface of a solid substrate contaminated by at least one biological species found on said surface and possibly under said surface in the depth of the substrate, in which at least one cycle is carried out comprising the following successive steps:

a) the gel according to the invention, as described above, is applied on said surface;

b) the gel is maintained on the surface at least for a sufficient time so that the gel destroys and/or inactivates and/or absorbs the biological species, and so that the gel dries and forms a dry and solid residue containing said biological species;

c) the dry and solid residue containing said biological species is removed.

It should be noted that, in the case of a non-porous surface, the <<inactivated>> biological contamination is recovered by the dry gel flakes.

On the other hand, in the case of a deep contamination, as this is the case in porous materials such as cement matrices, the dry gel will only contain the surface contamination residue.

The deep, internal, contamination, <<inactivated>> in situ following the action of the super-absorbent of the gel will remain in the core of the substrate, material.

Advantageously, the solid substrate is a porous substrate, preferably a porous mineral substrate.

However, the efficiency of the gel and of the method according to the invention is just as good in the presence of a non-porous and/or non-mineral surface.

Advantageously, the substrate is made of at least one material selected from metals such as stainless steel; polymers such as plastic materials or rubbers like poly(vinyl chloride)s or PVC, polypropylenes or PP, polyethylenes or PE notably high density polyethylenes or HDPE, poly (methyl methacrylate)s or PMMA, poly(vinylidene fluoride) s or PVDF, polycarbonates or PC; glasses; cements; mortars and concretes; plasters; bricks; natural or artificial stone; ceramics.

Advantageously, the biological species is selected from the toxic biological species already listed above.

Advantageously, the gel is applied on the surface to be decontaminated in an amount from 100 g to 2,000 g of gel per $m^2$ of surface, preferably from 500 to 1,500 g of gel per $m^2$ of surface, still preferably from 600 to 1,000 g per m2 of surface, which generally corresponds to a gel thickness deposited on the surface comprised between 0.5 mm and 2 mm.

Advantageously, the gel is applied on the solid surface by spraying, with a brush or with a hawk.

Advantageously (during step b)), the drying is achieved at a temperature from 1° C. to 50° C., preferably from 15° C.

to 25° C., and under relative humidity from 20% to 80%, preferably from 20% to 70%.

Advantageously, the gel is maintained on the surface for a duration from 2 to 72 hours, preferably from 2 to 48 hours, still preferably from 5 to 24 hours.

Advantageously, the dry and solid residue appears as particles, for example flakes, with a size from 1 to 10 mm, preferably from 2 to 5 mm.

Advantageously, the dry and solid residue is removed from the solid surface by brushing and/or suction.

Advantageously, the cycle described above may be repeated for example from 1 to 10 times by using the same gel during all the cycles or by using different gels during one or several cycles.

Advantageously, during step b), the gel, before total drying, is re-wetted with a solution of a biological decontamination agent, preferably with the solution of the biological active agent of the gel applied during step a) in the solvent of this gel.

During step b), the gel may, before total drying, be re-wetted with the biocidal solution contained in the biological decontamination gel already described above, which generally then avoids repeating of the application of the gel on the surface and causes saving of reagents and a limited amount of waste. This re-wetting operation may be repeated.

As a summary, the method and the gel according to the invention inter alia have the following advantageous properties:

application of the gel by spraying,
adherence to the walls,
obtaining the maximum decontamination efficiency at the end of the drying phase of the gel, including in a situation of penetrating contamination notably in the case of porous surfaces.

Generally, it is ensured that the drying time is longer than or equal to the time required for inactivation. In the case of deep inactivation, one generally resorts to re-wetting.

the treatment of a very wide range of materials,
the absence of any mechanical or physical alteration of the materials at the end of the treatment,
the application of the method under variable climate conditions,
reduction of the waste volume,
ease to recover the dry waste.

Other features and advantages of the invention will become better apparent upon reading the detailed description which follows, this description being made as an illustration and not as a limitation, in connection with the appended drawings.

SHORT DESCRIPTION OF THE DRAWINGS

Figures 4, 5:
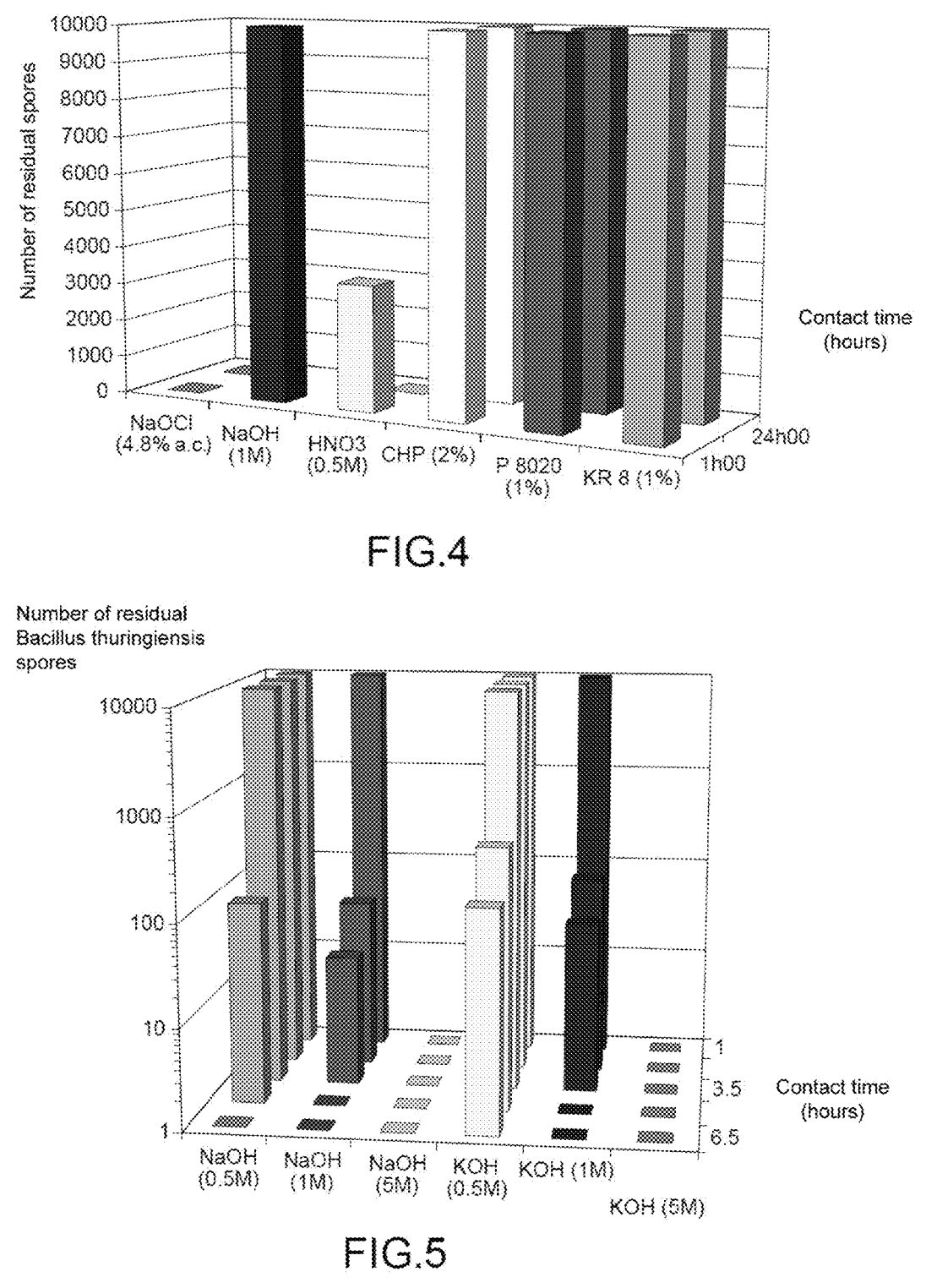

FIG. 4 is a graph which illustrates the kinetics for inhibiting spores of *Bacillus thuringiensis*, in different liquid biocidal solutions containing different active decontamination agents at various concentrations, i.e.: 4.8% NaOCl, 1M NaOH, 0.5M $HNO_3$, and 2% HPC (hexadecyl-pyridinium chloride); comparative solutions containing 1% of surfactant Pluronic® P 8020, or 1% of surfactant KR8 (ethoxylated fatty acid) are also tested. The number of residual spores is given for each of the biocidal solutions at contact times of 1 hour and 24 hours.

FIG. 5 is a graph which illustrates the kinetics for inhibiting spores of *Bacillus thuringiensis*, in different liquid biocidal solutions containing different bases at various concentrations, i.e.: 0.5M NaOH, 1M NaOH, 5M NaOH, 0.5M KOH, 1M KOH and 5M KOH. The number of residual spores is given for each of the biocidal solutions at contact times of 1 hour, 2 hours, 3 hours, 4 hours and 5 hours.

Figure 6:
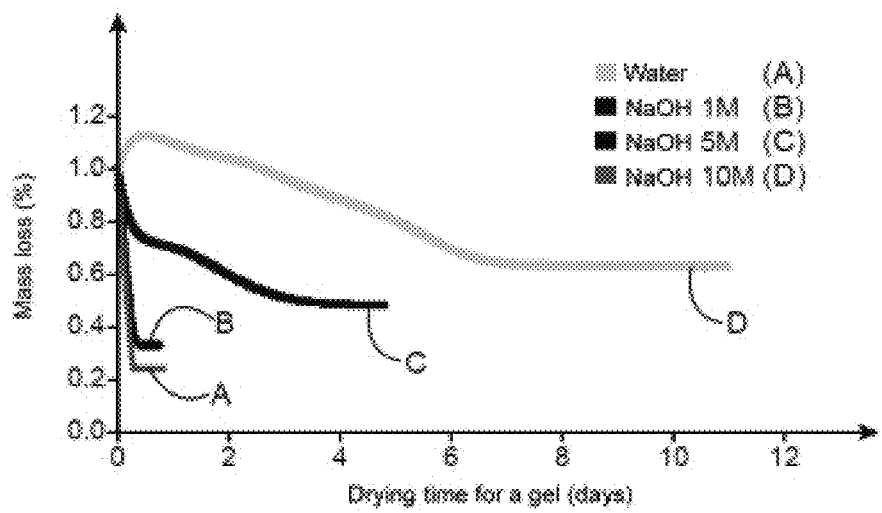

FIG. 6 is a graph which illustrates the influence of the sodium hydroxide concentration in the gel on the drying time.

The loss of mass of the gel in % is plotted in ordinates and the drying time of the gel in days is plotted in abscissas.

The curves A, B, C and D respectively illustrate the drying of the gel without NaOH (only with water), and with NaOH concentrations of 1M, 5M and 10M.

Figure 7:
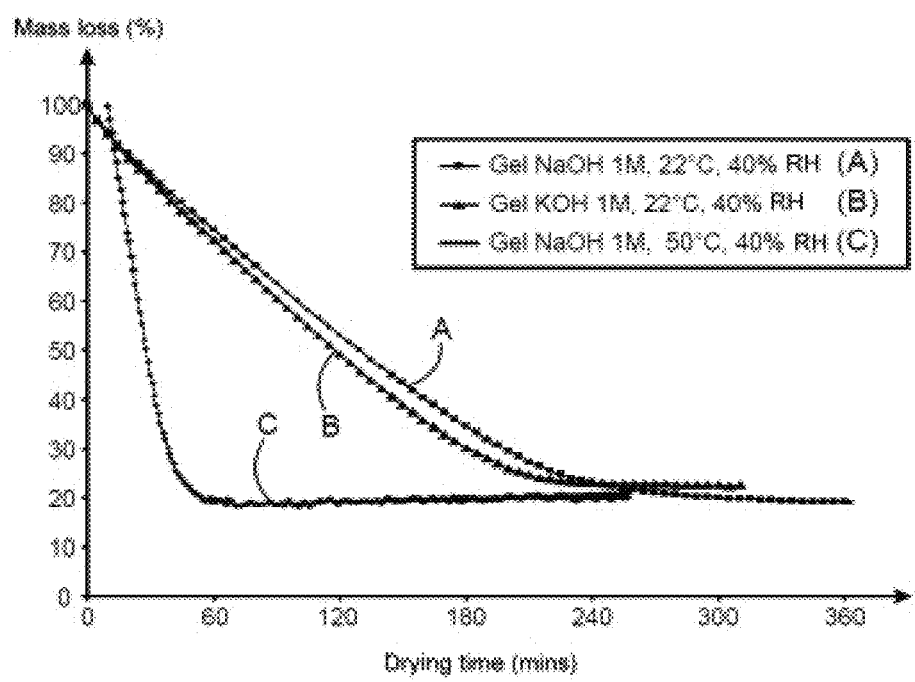

FIG. 7 is a graph which illustrates the influence of the temperature on the drying kinetics of a gel based on 1M NaOH; and the drying kinetics of a gel based on 1M KOH.

The loss of mass of the gel in % is plotted in ordinates and the drying time of the gel in minutes is plotted in abscissas.

Curve A illustrates the drying of a gel based on 1M NaOH at 22° C. and under a relative humidity of 40%, curve B illustrates drying of a gel based on 1M KOH at 22° C. and under a relative humidity of 40%, the curve C illustrates the drying of a gel based on 1M KOH at 50° C. and under a relative humidity of 40%.

Figure 8:
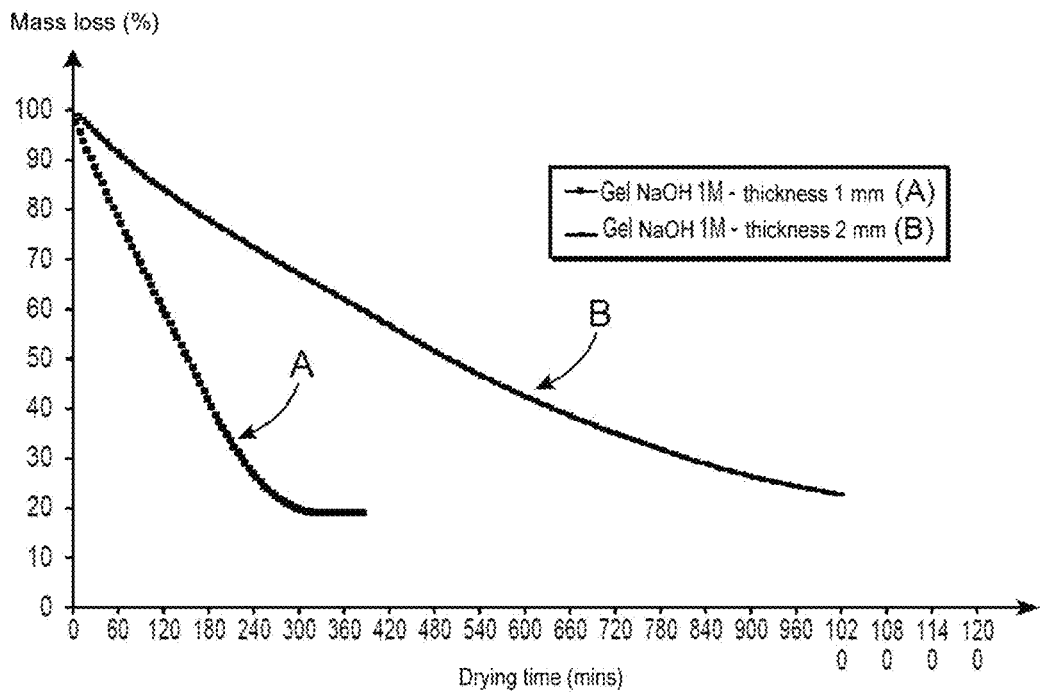

FIG. 8 is a graph which illustrates the influence of the deposited gel thickness on the drying kinetics of a gel based on 1M NaOH.

The loss of mass of the gel in % is plotted in ordinates and the drying time of the gel in minutes is plotted in abscissas.

Curve A illustrates the drying of a gel deposited on a thickness of 1 mm, and curve B illustrates the drying of a gel deposited on a thickness of 2 mm.

Figure 9:
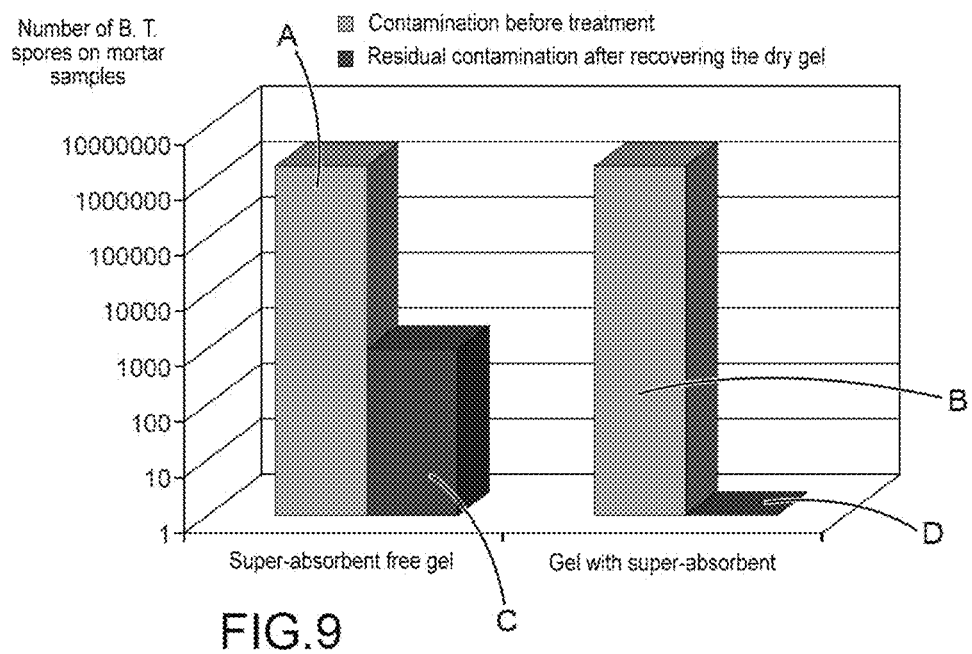

FIG. 9 is a graph which illustrates the influence of the super-absorbent polymer on the biological decontamination efficiency of a mortar, expressed by the number of spores of *Bacillus thuringiensis* on a mortar sample.

For each gel, the left bars (in pale grey A and B) represent the contamination of the mortar samples before treatment, and the right bars (in dark grey C and D) illustrate the residual contamination of the mortar samples after recovery of the dry gel.

The graph shows two distinct treatments by a gel, the first (left portion of the graph, bars A and C placed side by side on the left of the graph) in the presence of a biocidal gel free of any super-absorbent polymer, the second (right portion of the graph, bars B and D placed side by side on the right of the graph) in the presence of the same biocidal gel to which the super-absorbent polymer was added.

Figure 10:
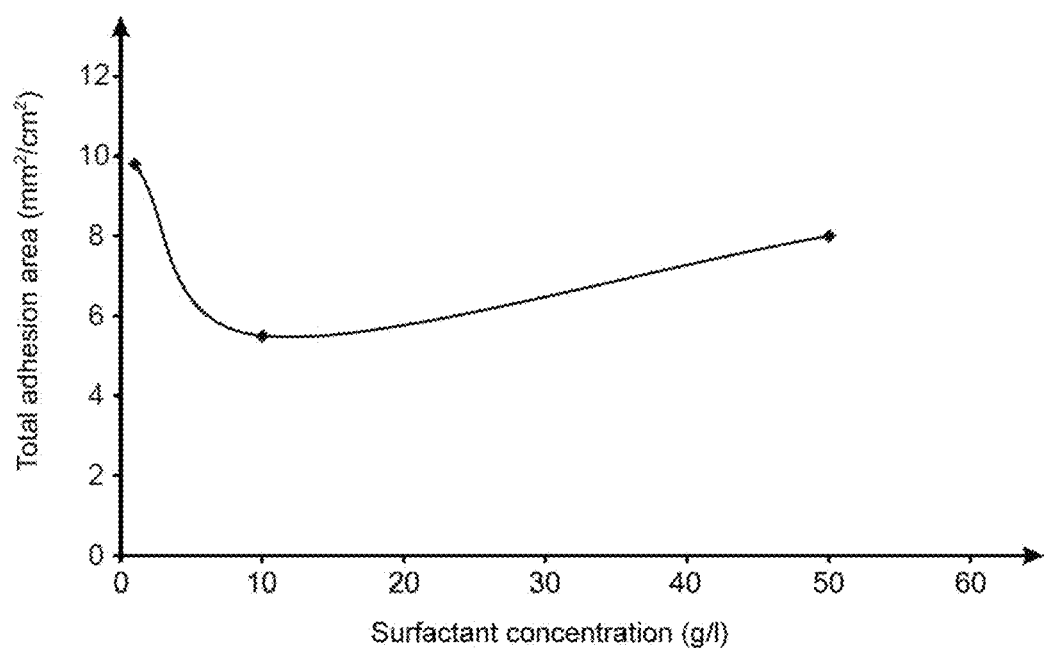

FIG. 10 is a graph which represents the influence of the surfactant (Pluronic®) concentration on the adhesion power of the dry gel flakes.

The total adhesion area ($mm^2/cm^2$), is plotted in ordinates, and the surfactant concentration (g/L) is plotted in abscissas.

Figure 11:
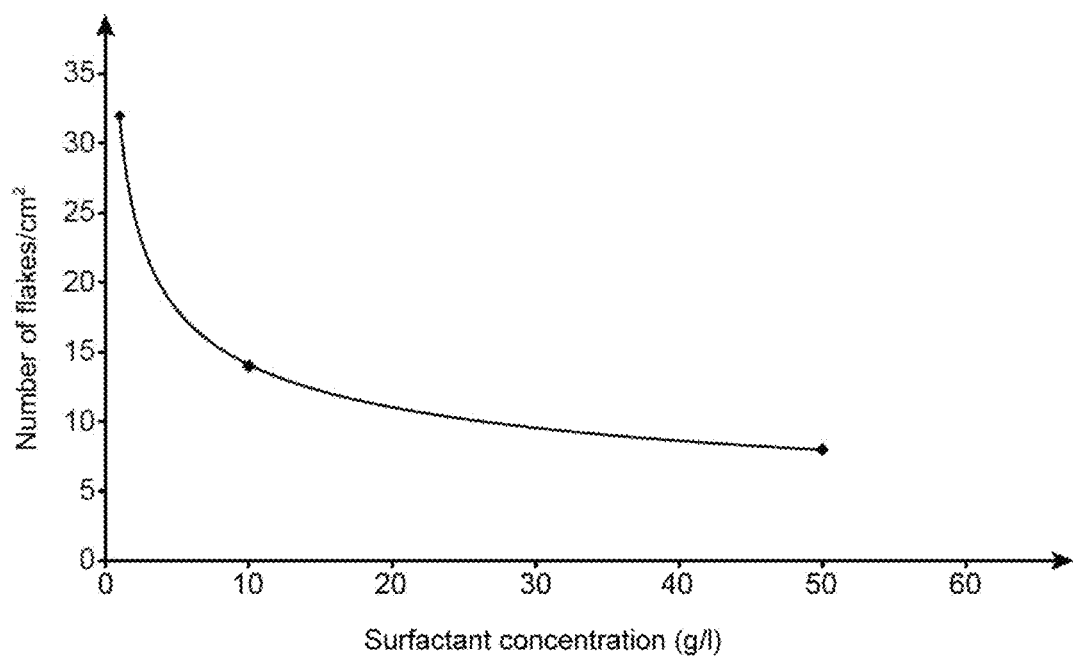

FIG. 11 is a graph which illustrates the influence of the surfactant (Pluronic®) concentration on the number of formed dry gel flakes.

The number of flakes/$cm^2$ is plotted in ordinates, and the surfactant concentration (g/L) is plotted in abscissas.

Figure 12:
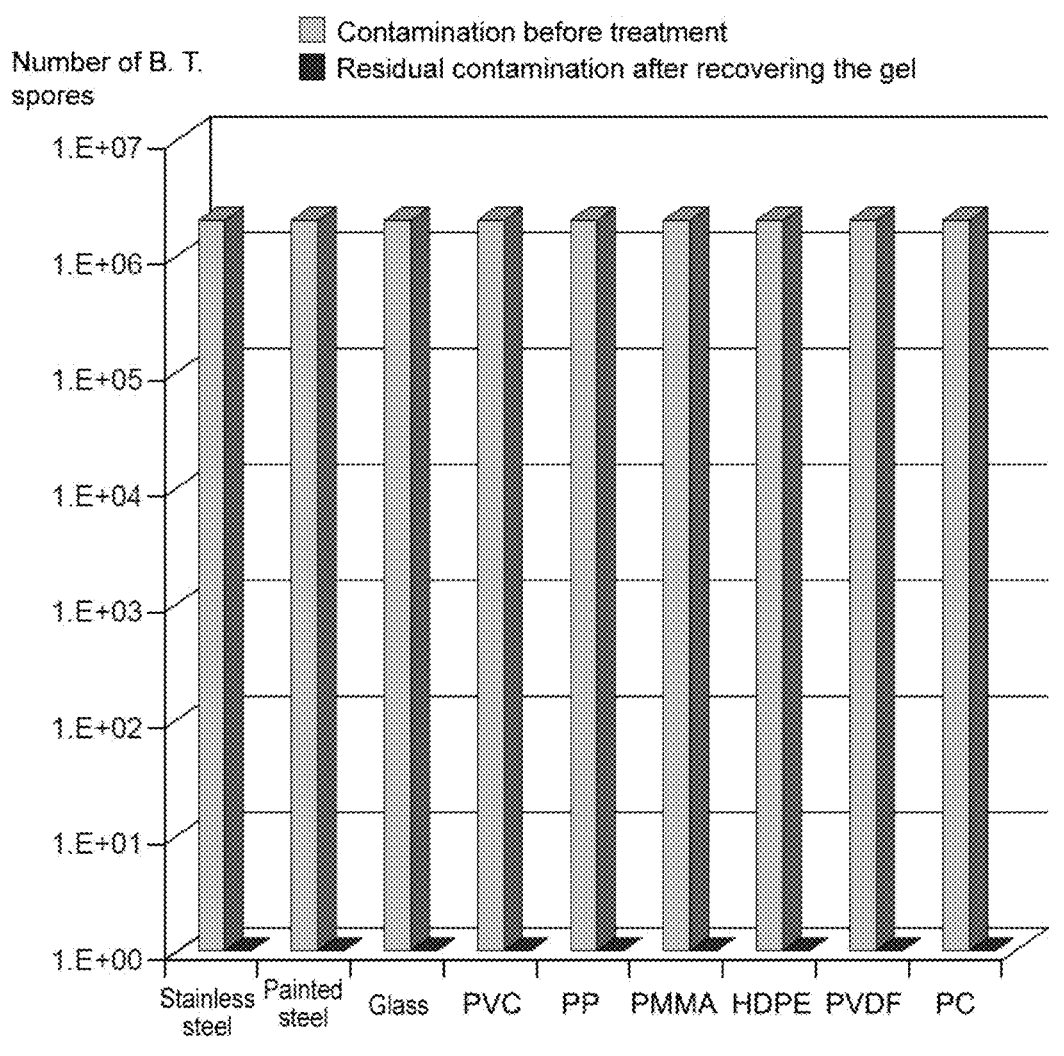

FIG. 12 is a graph which illustrates the efficiency of the gel according to the invention depending on the nature of the treated material.

The number of spores of *Bacillus thuringiensis* is plotted in ordinates.

For each material, the left bars (pale grey) represent the contamination before treatment by the gel according to the invention and the right bars (black) represent the residual contamination after recovery of the gel.

DETAILED DISCUSSION OF PARTICULAR EMBODIMENTS

The gel according to the invention may be easily prepared at room temperature.

For example, the gel according to the invention may be prepared, by adding preferably gradually, the inorganic viscosifying agent(s) for example the alumina(s) and/or the silica(s), to a solution containing the active biological decontamination agent(s), the surfactant(s) and the super-absorbent polymer(s).

This addition may be carried out by simply pouring the viscosifying agent(s) into said solution. Upon adding the inorganic viscosifying agent(s), the solution containing the active biological decontamination agent(s), the surfactant(s) and the super-absorbent polymer(s) is generally maintained under mechanical stirring. This stirring may for example be produced by means of a mechanical stirrer equipped with a three-blade propeller.

The stirring rate is generally comprised between 600 and 800 revolutions/minute.

After the end of the addition of the mineral viscosifying agent(s), stirring is further continued, for example for 2 to 5 minutes, so as to obtain a perfectly homogeneous gel.

It is quite obvious that other procedures for preparing gels according to the invention may be applied with addition of the components of the gel in a different order from the one mentioned above.

Generally, the gel according to the invention should have a viscosity of less than 200 mPa·s under shearing of 1,000 $s^{-1}$ so as to allow spraying onto the surface to be decontaminated, at a distance (for example at a distance from 1 to 5 m) or close (for example at a distance of less than 1 m, preferably from 50 to 80 cm). The recovery time of the viscosity should generally be less than one second and the viscosity under low shearing should be greater than 10 Pa·s so as not to run on the wall.

It should be noted that the surfactant of the gel according to the invention favorably and notably influences the rheological properties of the gel according to the invention. This surfactant notably gives the possibility that the gel according to the invention may be applied by spraying and avoids the risks of spreading or runoff when treating vertical surfaces and ceilings.

Figure 1:
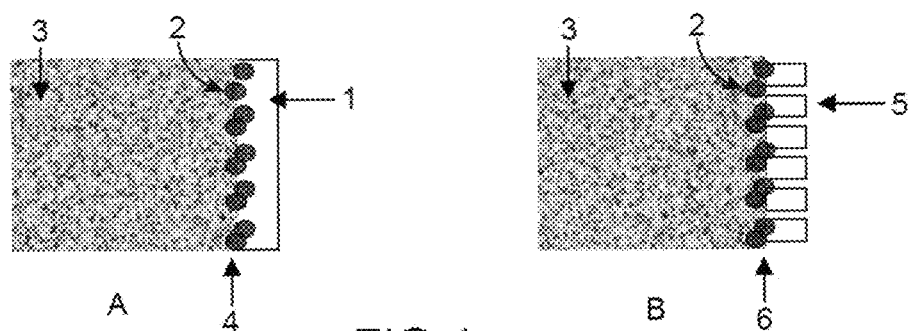
FIG. 1 (A, B) shows schematic sectional views illustrating the main steps of the method according to the invention for the decontamination of a solid material.

The thereby prepared gel according to the invention is then applied (1) (FIG. 1) on the solid surface (2) to be decontaminated of a substrate made of a solid material (3), in other words on the surface (2) having been exposed to biological contamination (4); this biological contamination (4) may consist in one or more of the biological species already defined above.

As this has already been indicated above, the active biological decontamination agent is selected depending on the biological species to be removed, destroyed or inactivated.

Except possibly for lightweight metal alloys of the aluminum type, in the case when basic or acid gels are applied, there is no limitation as to the material which constitutes the surface (2) to be decontaminated, indeed the gel according to the invention allows the treatment without any damage of all kinds of materials even fragile materials.

The gel according to the invention does not generate any alteration, erosion, chemical, mechanical or physical attack of the treated material. The gel according to the invention is therefore by no means detrimental to the integrity of the treated materials and even allows their reuse. Thus, sensitive equipment such as military equipment is preserved and may after their decontamination be reused, while monuments treated with the gel according to the invention are absolutely not degraded and their visual and structural integrity is found to be preserved.

This material of the substrate (3) may therefore be selected from metals such as stainless steel, from polymers such as plastic materials or rubbers among which mention may be made of PVC, PP, PE notably HDPE, PMMA, PVDF, PC, glasses, cements, mortars and concretes, plasters, bricks, natural or artificial stone, ceramics.

In any case (see Example 9 and FIG. 12), regardless of the material, the decontamination efficiency by the gel according to the invention is total.

The treated surface may be painted or non-painted.

In a particularly surprising way, it was found that the gel according to the invention was particularly efficient on porous materials such as cement matrices like slurries, mortars and concretes, bricks, plasters, or further natural or artificial stone. Indeed, the presence of the gel according to the invention of a super-absorbent polymer allows decontamination of the porous material over a much more substantial depth than with an equivalent gel without any super-absorbent polymer.

In other words, the presence of a super-absorbent polymer in the gel according to the invention facilitates diffusion of the active decontamination agent, for example of the biocidal agent into the depth of the material when the question is of treating porous substrates, especially porous mineral substrates.

The efficiency of the treatment with the gel according to the invention is generally total, including on materials contaminated over several millimeters of depth.

Also there does not exist any limitation as to the shape, the geometry and the size of the surface to be decontaminated, the gel according to the invention and the method applying it allows treatment of large size surfaces, of surfaces having complex geometries, for example having recesses, angles, nooks.

The gel according to the invention ensures efficient treatment not only of horizontal surfaces such as floors, but also of vertical surfaces such as walls, or of tilted slant or overhanging surfaces such as ceilings.

As compared with existing biological decontamination methods which apply liquids such as solutions, the decontamination method according to the invention which applies a gel is particularly advantageous for treating large surface area materials which are non-transportable and implanted outdoors. Indeed, the method according to the invention because of the application of a gel, allows decontamination in situ while avoiding the spreading of chemical solutions into the environment and dispersion of the contaminating species.

The gel according to the invention may be applied on the surface to be treated by all the application methods known to the man skilled in the art.

Standard methods are spraying for example with a gun or application by means of a brush or a hawk.

For application of the gel according to the invention by spraying it on the surface to be treated, the colloidal solution may for example be conveyed via a low pressure pump, for example a pump which applies a pressure of less than or equal to 7 bars i.e. about $7.10^5$ Pascals.

The bursting of the gel jet on the surface may for example be obtained by means of a flat jet nozzle or of a round jet nozzle.

The distance between the pump and the nozzle may be any distance, for example it may be from 1 to 50 m, notably from 1 to 25 m.

The sufficiently short time for recovering viscosity of the gels according to the invention allows the sprayed gels to adhere to all the surfaces, for example to walls.

The amount of gel deposited on the surface to be treated is generally from 100 to 2,000 $g/m^2$, preferably from 500 to 1,500 $g/m^2$, still preferably from 600 to 1,000 $g/m^2$.

The amount of gel deposited per unit surface and consequently the thickness of the deposited gel, have an influence on the drying rate.

Thus, when a film, layer of gel with a thickness from 0.5 mm to 2 mm is sprayed onto the surface to be treated, the efficient contact time between the gel and the material is then equivalent to its drying time, a period during which the active ingredient contained in the gel will interact with the contamination.

In the case of porous substrates, for example cement matrices, the action time of the biocidal solution having penetrated into the core of the material following the action of the super-absorbent polymer may be longer than the drying time of the gel, in which case, it is generally necessary either to perform re-wetting with the biocidal solution, or to repeat spraying of the gel.

Further, it was shown surprisingly that the amount of gel deposited when it is located in the ranges mentioned above and in particular when it is greater than 500 $g/m^2$ and notably in the range from 500 to 1,500 $g/m^2$, which corresponds to a minimum thickness of deposited gel for example greater than 500 µm for an amount of deposited gel of more than 500 $g/m^2$, allowed, after drying of the gel, gel fracturation to be obtained in the form of millimetric flakes, for example with a size from 1 to 10 mm, preferably from 2 to 5 mm, which may be sucked up.

The amount of deposited gel and therefore the thickness of the deposited gel, preferably greater than 500 $g/m^2$ i.e. 500 µm, is the fundamental parameter which influences the size of the dry residues formed after drying of the gel and which thus ensures that dry residues of millimetric size and not powdery residues are formed, such residues being easily removed by a mechanical method and preferably by suction.

However, it should also be noted that by means of the low concentration surfactant, the drying of the gel is improved and leads to a homogeneous fracturation phenomenon with a mono-dispersed size of the dry residues and an increased capability of the dry residues to be detached from the support.

The gel is then maintained on the surface to be treated for the whole time required for its drying. During this drying step, which may be considered to form the active phase of the method according to the invention, the solvent contained in the gel, i.e. generally the water contained in the gel evaporates until a dry and solid residue is obtained.

The drying time depends on the composition of the gel in the concentration ranges of its constituents given above, but also, as this has already been specified, on the amount of deposited gel per unit surface, i.e. on the thickness of the deposited gel.

The drying time also depends on the weather conditions i.e. on the temperature and relative humidity of the atmosphere in which the solid surface is found.

The method according to the invention may be applied under extremely wide weather conditions, i.e. at a temperature T from 1° C. to 50° C. and at a relative humidity HR from 20% to 80%.

The drying time of the gel according to the invention is therefore generally from 1 hour to 24 hours at a temperature T from 1° C. to 50° C. and at a relative humidity HR from 20% to 80%.

It should be noted that the formulation of the gel according to the invention essentially because of the presence of surfactants such as the <<Pluronics®>> generally ensures a drying time which is substantially equivalent to the contact time (between the decontamination agent, such as a biocidal agent, and the biological, notably biotoxic species to be removed) which is necessary, required for inactivating and/or absorbing the contaminating species polluting the material. In other words, the formulation of the gel ensures a drying time which is none other than the inactivation time of the biological contaminating species and which is compatible with the kinetics for inhibiting biological contamination.

The specific surface area of the mineral filler generally used is generally from 50 $m^2/g$ to 300 $m^2/g$, preferably of 100 $m^2/g$ and the absorption capacity of the gel according to the invention gives the possibility of trapping the labile (surface) contamination of the material constituting the surface to be treated.

If necessary, the contaminating biological species are inactivated in the gelled phase. After drying of the gel, the inactivated contamination is removed during the recovery of the dry gel residue, as described below.

At the end of the drying of the gel, the gel fractures in a homogeneous way so as to give millimetric solid dry residues, for example with a size from 1 to 10 mm, preferably from 2 to 5 mm, non-powdery, generally in the form of solid flakes (5).

The dry residues may contain the inactivated contaminating species (6).

The dry residues such as flakes (5), obtained at the end of the drying have low adherence to the surface (2) of the decontaminated material. Consequently, the dry residues obtained after drying the gel may be easily recovered by simple brushing and/or suction. However, the dry residues may also be evacuated by a gas jet, for example a jet of compressed air.

Thus, no rinsing is necessary and the method according to the invention does not generate any secondary effluent.

The method according to the invention therefore thus first of all produces significant savings in chemical reagents as compared with a decontamination method by washing with a solution. Next, because a waste in the form of a dry residue which may be directly sucked up, is obtained, a rinsing operation with water or with a liquid is avoided. Of course the result of this is a decrease in the amount of effluent produced but also a notable simplification in terms of treatment facility channel and outlet; exutory.

Due to the predominantly majority mineral composition of the gel according to the invention and to the small amounts of produced waste, the dry wastes may be stored or directed to a discharge facility channel without any preliminary treatment.

As example, in the common case when 1,000 grams of gel per $m^2$ of treated surface are applied, the dry waste mass produced is less than 300 grams per $m^2$.

Figure 2:
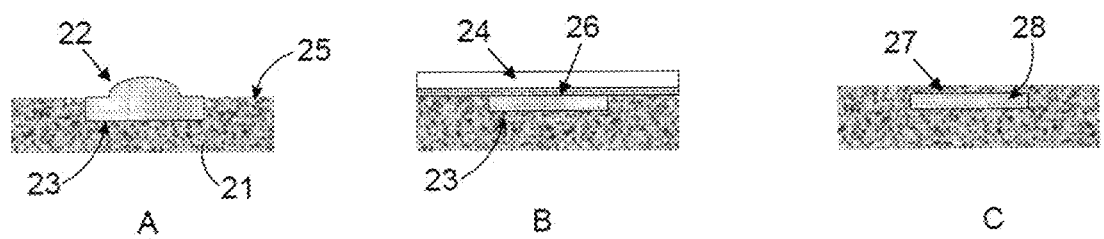
FIG. 2 (A, B, C) shows schematic sectional views showing the mode of action of a gel without any super-absorbent polymer on a cement material contaminated in depth by a contamination in liquid form.

In FIG. 2, decontamination with a gel non-compliant with the invention not containing any super-absorbent polymer, of a porous substrate (21) contaminated by spores in an aqueous solution (22) is illustrated. The contamination front (23) extends into the depths of the substrate (FIG. 2A). When a biocidal gel (24) is applied on the surface (25) of the substrate, the diffusion front (26) of the biocidal agent extends very little into the depth of the substrate and remains behing, before the contamination front (23) (FIG. 2B). Consequently, when the gel is removed (FIG. 2C), the cleaned-up area (27) extends very little in depth and there remains a residual contamination (28) in the porous substrate (21).

Figure 3:
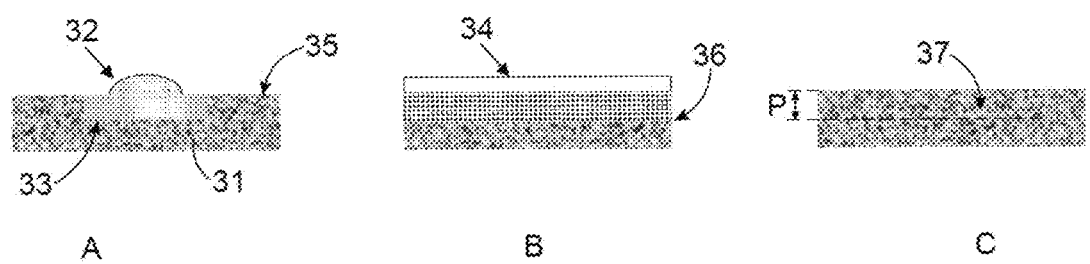
FIG. 3 (A, B, C) shows schematic sectional views showing the mode of action of a gel containing a super-absorbent polymer on a cement material contaminated in depth by a contamination in liquid form.

In FIG. 3, the decontamination by a gel according to the invention containing a super-absorbent polymer, of a porous substrate (31) contaminated with spores in an aqueous solution (32) is illustrated. The contamination front (33) extends into the depth of the substrate (FIG. 3A). When a biocidal gel containing the super-absorbent polymer (34) is applied on the surface (35) of the substrate, the diffusion front (36) of the biocidal agent extends into the depth of the substrate and goes beyond the contamination front (FIG. 3B). Consequently, the cleaned-up area (37) extends in depth (P) and there no longer remains any residual contamination in the porous substrate.

The invention will now be described with reference to the following examples, given as an illustration and not as a limitation.

EXAMPLES

Example 1

In this example, the kinetics for inhibiting spores of Bacillus thuringiensis are studied, in different liquid biocidal solutions containing different active decontamination agents at various concentrations, i.e.: 4.8% NaOCl, 1M NaOH; 0.5 $HNO_3$, 2% HPC (hexadecyl pyrdinium chloride). Comparative solutions containing the surfactant Pluronic® P 8020 at 1%, or the surfactant KR8 (ethoxylated fatty alcohol) at 1% were also used.

Experimental Procedure:

The experiment consists of putting, with stirring, $2 \times 10^6$ spores in contact with 1 ml of liquid biocidal solution.

At the end of 1 hour and of 24 hours of stirring, samples were taken in order to reveal the biological activity of the mixture. The development, revelation then consists of depositing a drop of mixture on a nutritive medium (agar gel) and of counting, at the end of an incubation period of 16 hours at 30° C., the number of colonies formed. Each of the colonies being the result of an inactivated spore.

The results of the tests are given in FIG. 4 wherein the number of residual spores is given for each of the biocidal solutions and of the comparative solutions at contact times of 1 hour and of 24 hours.

FIG. 4 notably shows that Pluronic® P 8020 and the surfactant KR8 do not have any action on the spores.

Example 2

In this example, the kinetics of inhibition of spores of Bacillus thuringiensis are studied, in various liquid biocidal solutions containing different bases at various concentrations, i.e. 0.5M NaOH, 1M NaOH; 5M NaOH, 0.5M KOH, 1M KOH and 5M KOH.

The experimental procedure used is similar to the one described above in Example 1. Only the number of mixture samplings is increased (1 hour, 2 hours, 3 hours, 4 hours, 5 hours) so as to determine the kinetics for inhibiting the spores in the relevant biocidal medium.

The results of the tests are given in FIG. 5 where the number of residual spores is given for each of the biocidal solutions at contact times of 1 hour, 2 hours, 3 hours, 4 hours, 5 hours.

FIG. 5 shows that the increase in the concentration of biocidal agent gives the possibility of considerably increasing the inhibition rates of the spores of Bacillus thuringiensis.

Example 3

In this example, the influence of the sodium hydroxide concentration on the drying time in a gel of the present invention is studied.

The gel has the following composition in mass percentages:
Alumina: 14%
Sodium hydroxide solution (variable concentration): 85%
Surfactant (Pluronic® P8020): 0.7%
Super-absorbent polymer: Sodium polyacrylate Norsocryl® S35: 0.3%.

Experimental Procedure:

The gels with a variable sodium hydroxide concentration (0 M, 1 M, 5 M and 10 M) are spread out on an inert metal support over a controlled thickness of 1 mm. The metal support containing the gel film is then placed in a weathering, climatic, enclosure equipped with a precision balance which ensure the tracking of the mass loss of the gel over time. The weathering enclosure is regulated to a temperature of 22° C. and to a relative humidity of 60%.

The curves of FIG. 6 show that the hygroscopicity of sodium hydroxide (but also of potassium hydroxide) slows down the drying phenomenon of the gel. Consequently, the contact time between the decontamination agent, i.e. the biocidal solution, and the biological contamination is considerably increased.

Example 4

In this example, the influence of temperature on the drying kinetics of a gel based on 1M NaOH; and on the drying kinetics of a gel based on 1M KOH, is studied.

The gels have the following composition in mass percentages:
Alumina: 14%
Sodium hydroxide solution (1M): 85%
Surfactant(Pluronic® P8020): 0.7%
Super-absorbent polymer: Sodium polyacrylate Norsocryl® S35: 0.3%.
Or else,
Alumina: 14%
Potassium hydroxide solution (1M): 85%
Surfactant(Pluronic® P8020): 0.7%
Super-absorbent polymer: Sodium polyacrylate Norsocryl® S35: 0.3%.

The experimental procedure used is similar to the one described above in Example 3. The weathering enclosure is in one case regulated to a temperature of 22° C. and to 40% of relative humidity (gel with 1 M NaOH, gel with KOH 1 M), in another case to a temperature of 50° C. and 40% of relative humidity (gel with 1 M NaOH, left curve C).

The curves of FIG. 7 show that the drying time of the gel based on 1M NaOH at 22° C. is slightly longer than that of the gel based on 1M KOH at the same temperature, while the drying time of the gel with 1M NaOH at 50° C. is strongly reduced.

Example 5

In this example, the influence of the thickness of the deposited gel on the kinetics for drying a gel of the present invention based on 1M NaOH is studied.

The gel has the following composition in mass percentages:
Alumina: 14%
Sodium hydroxide solution (1M): 85%
Surfactant (Pluronic® P8020): 0.7%
Super-absorbent polymer: Sodium polyacrylate Norsocryl® S35: 0.3%.

The experimental procedure used is similar to the one described above in Example 3. The weathering enclosure is in this case regulated to a temperature of 22° C. and to 40% of relative humidity. Only the thickness of the gel deposited on the metal support varies from 1 mm to 2 mm.

The curves of FIG. 8 show that the drying time is clearly extended when passing from a thickness of deposited gel of 1 mm (curve A) to a thickness of deposited gel of 2 mm (curve B).

Example 6

In this example, the influence of the super-absorbent polymer on the efficiency of the biological decontamination of a mortar, expressed by the number of spores of *Bacillus thuringiensis* on a mortar sample is studied.
Experimental Procedure:

The mortar samples are contaminated by depositing a drop of water with a volume of 100 μl containing $2\times10^7$ spores of *Bacillus thuringiensis.*

After diffusion of the contaminating solution into the depth of the cement material, the biocidal decontamination gels are spread out on the contaminated face of the mortar samples. The amount of deposited gel is equal to 1,000 g/$m^2$.

At the end of 24 hours of drying, the formed dry gel flakes are removed from the mortar sample. The latter is then immersed in a nutritive solution Luria Broth maintained under stirring for 3 hours at a temperature of 37° C.

Development, revelation of the residual biological activity of the mortar samples then consists of sampling a known volume of nutritive solution Luria Broth in which the mortar samples have soaked and of depositing it on agarose gel. After 24 hours of incubation, by counting the colonies of bacteria it is possible to reveal the number of spores non-inactivated by the biocidal decontamination gel.

The gel free comprising a super-absorbent polymer has the following composition in mass percentages:

Alumina: 14%

Sodium hydroxide solution (1M): 85%

Surfactant (Pluronic® P8020): 0.7%

Super-absorbent polymer: Sodium polyacrylate Norsocryl® S35: 0.3%

The gel free of absorbent polymer has the same composition except that the super-absorbent polymer is omitted.

The graph of FIG. 9 shows that the addition of a super-absorbent polymer gives the possibility of significantly increasing the efficiency of the decontamination of a porous material such as a mortar which is contaminated in depth over a thickness of several millimeters.

Example 7

In this example, the influence of the surfactant Pluronic® P 8020 concentration on the adhesion potential of the dry gel flakes is studied.

Experimental Procedure:

The gel is applied on a flexible stainless steel blade (a calibrated sheet from Outillage francilien), for which the mechanical properties are known (25 μm thick, length of 2 cm, width of 1 cm and a Young's modulus of $2.10^{11}$ Pa), one of the ends is fixed and the other is free. The surface of the gel layer is leveled with a suitable scraper so as to deposit a constant thickness of 1 mm thereon.

Two cameras are added, one camera placed above the gel layer gives the possibility of viewing the occurrence of the fractures and another one placed on the side gives the possibility of measuring the change in the thickness of the gel layer over time. The adhesion of the flakes is studied by analysis of the images obtained by both cameras.

The studied gel is the gel without any super-absorbent polymer in which the surfactant concentration is varied. The other compounds are maintained at mass contents equal to those of Example 6.

The surfactant concentrations are 0, 10 g/L, and 50 g/L.

The graph of FIG. 10 shows that in the range of concentrations which are of interest to us (<10 g/L), the increase in the concentration of Pluronic® generates a decrease in the adhesion of the flakes. The recovery of the dry gel waste by brushing and/or suction is then found to be facilitated.

Example 8

In this example, the influence of the surfactant concentration i.e. Pluronic® P 8020, on the number of formed dry gel flakes is studied.

The studied gel is the gel of Example 7 in which the surfactant concentration is varied.

The surfactant concentrations are 0, 10 g/L and 50 g/L.

The experimental procedure used is strictly the same as the one used in Example 7.

The graph of FIG. 11 shows that the addition of Pluronic® to the formulation of the gel generates a decrease in the number of flakes. The addition of Pluronic® gives the possibility of improving the toughness of the gelled matrix against the fracturation induced by the drying: the gel will fracture with more difficulty, the number of fractures will be less and the number of flakes will thus be smaller. As regards the decontamination method, the decrease in the number of flakes is a benefit: as the flakes are larger, the waste will be non-powdery during the phase for recovering the waste by brushing and/or suction.

Example 9

In this example, the efficiency of the treatment gel according to the invention on a contamination by spores of *Bacillus thuringiensis* is studied according to the nature of the treated material.

The studied gel is the gel comprising an absorbent polymer of Example 6.

The experimental procedure is identical with that of Example 6. As the studied materials are non-porous materials, the latter are treated with the gel after a 30 minute phase for evaporating the contaminating drop. This evaporation phase corresponds to the desire of treating a dried contamination, a priori the most harmful for the method of the invention, covering the surface of the materials.

The graph of FIG. 12 shows that after recovering the gel, regardless of the treated material (stainless steel, painted steel, glass, PVC, PP, PMMA, HDPE, PVDF, PC), the decontamination is total without the material being altered.

This example shows the efficiency and the versatility of the gel according to the invention.

REFERENCES

[1] JENEVEIN. E, "Cleaning composition for neutralizing biological and chemical weapons removal agents", U.S. Pat. No. 7,026,274 B2.

[2] SCHILLING. A, HODGE. R "Peracid-based large area decontamination", Patent No. US-A1-2006/0073067.

[3] CONERLY. L, EHNTHOLT. D, LOUIE. A, WHELAN. R "Chemical and/or biological decontamination system", US-A1-2003/0109017.

[4] TUCKER. M, COMSTOCK. R "Decontamination formulation with sorbent additive", US-A1-2004/0022867.

[5] ROGERS. J. V, SABOURIN. C. L. K, CHOI. Y. W "*Decontamination assessment of bacillus subtilis, and Geobacillus stearothermophilus spores on indoor surfaces using a hydrogen peroxide gas generator*", 2005.

[6] JOSSE. D, BOUDRY. I, NAUD. N "*Décontamination cutanée vis-à-vis des agents organophosphorés et de l'ypérite au soufre: Bilan et perspectives*", Médecine et armées, Vol. 34, No. 1, pages 33-36, 2006.

[7] HOFFMAN. D, Mc GUIRE. R "Oxidizer gels for detoxification of chemical and biological agents", U.S. Pat. No. 6,455,751 B1.

[8] HARPER. B, LARSEN. L "*A comparison of decontamination technologies for biological agents on selected commercial surface materials*", Biological weapons improved response program, April 2001.

[9] FAURE. S, FOURNEL. B, FUENTES. P, LALLOT. Y. "Procédé traitement d'une surface par un gel de traitement, et gel de traitement", FR-A1-2 827 530.

[10] FAURE. S, FUENTES. P, LALLOT. Y. "Gel aspirable pour la décontamination de surfaces et utilisation", FR-A1-2 891 470.

The invention claimed is:

1. A method for biological decontamination of a surface of a solid substrate contaminated by at least one biological species found on said surface and possibly under said surface in the depth of the substrate, wherein at least one cycle is carried out, consisting essentially of the following successive steps:
   a) applying a biological decontamination gel, consisting of a colloidal solution comprising: from 5 to 30% by mass based on the mass of the gel, of at least one inorganic viscosifying agent; from 0.5 to 10 mol/L of gel, of at least one active biological decontamination agent; 0.05 to 5% by mass based on the mass of the gel, of at least one super absorbent polymer; 0.1 to 2% by mass, based on the mass of the gel, of at least one surfactant; and the remainder of solvent; on said surface;
   b) maintaining the gel on the surface at least for a sufficient time so that the gel destroys and/or inactivates and/or absorbs the biological species, and so that the gel dries and forms a dry and solid residue containing said biological species;
   c) removing the dry and solid residue containing said biological species.

2. The method according to claim 1, wherein the solid substrate is a porous substrate.

3. The method according to claim 1, wherein the substrate is made of at least one material selected from metals; polymers; glasses, cements; mortars and concretes; plasters; bricks; natural or artificial stone; and ceramics.

4. The method according to claim 1, wherein the biological species is selected from bacteria, fungi, yeasts, viruses, toxins, spores and protozoans.

5. The method according to claim 1, wherein the biological species is selected from bio-toxic species.

6. The method according to claim 5, wherein said bio-toxic species are selected from pathogenic spores, toxins, and viruses.

7. The method according to claim 6, wherein said pathogenic spores are selected from the spores of *Bacillus anthracis*, and said toxins are selected from *Botulinum* toxin.

8. The method according to claim 1, wherein the gel is applied on the surface in an amount from 100 g to 2,000 g of gel per $m^2$ of surface.

9. The method according to claim 1, wherein the gel is applied on the solid surface by spraying, with a brush or with a hawk.

10. The method according to claim 1, wherein, during step b), the drying is carried out at a temperature from 1° C. to 50° C., and under a relative humidity from 20% to 80%.

11. The method according to claim 1, wherein the gel is maintained on the surface for a duration from 2 to 72 hours.

12. The method according to claim 1, wherein the dry and solid residue appears as particles with a size from 1 to 10 mm.

13. The method according to claim 1, wherein the dry and solid residue is removed from the solid surface by brushing and/or suction.

14. The method according to claim 1, wherein the described cycle is repeated from 1 to 10 times by using the same gel during all the cycles or by using different gels during one or more cycle(s).

15. The method according to claim 1, wherein, during step b), the gel, before total drying, is re-wetted with a solution of a biological decontamination agent.

16. The method according to claim 1, wherein the inorganic viscosifying agent is selected from aluminas, silicas, aluminosilicates, clays and mixtures thereof.

17. The method according to claim 16, wherein the inorganic viscosifying agent is selected from pyrogenated silicas, precipitated silicas, hydrophilic silicas, hydrophobic silicas, acid silicas, basic silicas, and mixtures thereof.

18. The method according to claim 17, wherein the inorganic viscosifying agent consists of a mixture of a precipitated silica and a pyrogenated silica.

19. The method according to claim 17, wherein the inorganic viscosifying agent consists of one or more alumina(s) representing from 5 to 30% by mass, based on the mass of the gel.

20. The method according to claim 19, wherein the inorganic viscosifying agent consists of one or more alumina(s) representing from 8 to 17% by mass, based on the mass of the gel.

21. The method according to claim 1, wherein the active biological decontamination agent is selected from bases; acids; oxidizing agents; quaternary ammonium salts; and mixtures thereof.

22. The method according to claim 21, wherein said bases are selected from the group consisting of sodium hydroxide, potassium hydroxide, and mixtures thereof.

23. The method according to claim 21, wherein said acids are selected from the group consisting of nitric acid, phosphoric acid, hydrochloric acid, sulfuric acid, and mixtures thereof.

24. The method according to claim 21, wherein said oxidizing agents are selected from the group consisting of peroxides, permanganates, persulfates, ozone, hypochlorites and mixtures thereof.

25. The method according to claim 21, wherein said quaternary ammonium salts are selected from the group consisting of hexacetylpyridinium salts.

26. The method according to claim 1, wherein the super absorbent polymer is selected from sodium poly(meth)acrylates, starches grafted with a (meth)acrylic polymer, hydrolyzed starches grafted with a (meth)acrylic polymer; polymers based on starch, on gum, and on a cellulose derivative; and mixtures thereof.

27. The method according to claim 1, wherein the surfactant is selected from non ionic surfactants; and mixtures thereof.

28. The method according to claim 27, wherein said non ionic surfactants are selected from the group consisting of block copolymers; ethoxylated fatty acids; and mixtures thereof.

29. The method according to claim 28, wherein said block copolymers are copolymers of ethylene oxide and of propylene oxide.

30. The method of claim 10, wherein the solvent is selected from water, organic solvents and mixtures thereof.

* * * * *

UNITED STATES PATENT AND TRADEMARK OFFICE
CERTIFICATE OF CORRECTION

| | | |
|---|---|---|
| PATENT NO. | : 9,451,765 B2 | Page 1 of 1 |
| APPLICATION NO. | : 13/806856 | |
| DATED | : September 27, 2016 | |
| INVENTOR(S) | : Frederic Cuer et al. | |

It is certified that error appears in the above-identified patent and that said Letters Patent is hereby corrected as shown below:

Specification

Column 8, line 64: "IM-50005" should be --IM-5000S--.

Column 9, line 6: "carboxymethylcellulose said under" should be --carboxymethylcellulose sold under--.

Column 9, line 8: "polyglutamate said under" should be --polyglutamate sold under--.

Signed and Sealed this
Fifteenth Day of November, 2016

Michelle K. Lee
*Director of the United States Patent and Trademark Office*